(12) United States Patent
Lee et al.

(10) Patent No.: US 10,227,586 B2
(45) Date of Patent: Mar. 12, 2019

(54) GENOME-ORIGINATED ARTIFICIAL NCRNA EXPRESSION LIBRARY AND METHOD OF PREPARING THE SAME

(71) Applicant: KOREA ADVANCED INSTITUTE OF SCIENCE AND TECHNOLOGY, Daejeon (KR)

(72) Inventors: Younghoon Lee, Daejeon (KR); Won Kyong Kim, Daejeon (KR); Geunu Bak, Daejeon (KR); Hongmarn Park, Daejeon (KR); Jee Soo Choi, Daejeon (KR); Shinae Suk, Daejeon (KR); Ji Young Lee, Daejeon (KR); Yeongseong Yoon, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/491,154

(22) Filed: Apr. 19, 2017

(65) Prior Publication Data

US 2018/0044666 A1 Feb. 15, 2018

(30) Foreign Application Priority Data

Aug. 11, 2016 (KR) .................. 10-2016-0102606

(51) Int. Cl.
*C12N 15/10* (2006.01)

(52) U.S. Cl.
CPC ..... *C12N 15/1079* (2013.01); *C12N 15/1093* (2013.01)

(58) Field of Classification Search
None
See application file for complete search history.

(56) References Cited

U.S. PATENT DOCUMENTS

| 2003/0119014 A1* | 6/2003 | Donner | C12Q 1/6837 |
| | | | 435/6.11 |
| 2003/0143599 A1* | 7/2003 | Makarov | C12Q 1/6844 |
| | | | 435/6.16 |
| 2005/0260655 A1* | 11/2005 | Liu | C12N 15/1027 |
| | | | 435/6.12 |
| 2016/0186169 A1* | 6/2016 | Lee | C12N 15/113 |
| | | | 435/471 |

FOREIGN PATENT DOCUMENTS

| KR | 10-2014-0006369 | 1/2014 |
| KR | 10-2016-0083771 | 7/2016 |
| WO | 2009-012644 | 1/2009 |

OTHER PUBLICATIONS

Bak et al. ( Ponchon L. (eds) RNA Scaffolds. Methods in Molecular Biology, vol. 1316. Humana Press, New York, NY(2015): 211-225) (Year: 2015).*
Lee Young Hoon, "Regulation of stress through bacterial ncRNA", Intelligent Biodesignering a Powerful Tool for Revolution in Biotechnology, pp. 1-12 , Aug. 12, 2014.
Hongmarn Park et al., "Exploring sRNA-mediated gene silencing mechanisms using artificial small RNAs derived from a natural RNA scaffold in *Escherichia coli*", Nucleic Acids Research, Feb. 2013, vol. 41, No. 6, 3787-3804 from.
Hongmarn Park et al., "Effects of different target sites on antisense RNA-mediated regulation of gene expression", BMB Reports, Nov. 30 2014, 47(11): 619-624.
Geunu Bak et al., "An Effective Method for Specific Gene Silencing in *Escherichia coli* Using Artificial Small RNA", Methods in Molecular Biology, 2015 vol. 1316, 211-225.

* cited by examiner

*Primary Examiner* — Tracy Vivlemore
*Assistant Examiner* — Sahana S Kaup
(74) *Attorney, Agent, or Firm* — Lex IP Meister, PLLC

(57) ABSTRACT

The present invention relates to an artificial ncRNA expression library and a method for preparing the same, and particularly the present invention relates to a library securing the stability of the artificial ncRNA by cloning random fragmented DNA that whole genome DNA of *E. coli* is randomly fragmented to a middle of RNA scaffold having a double stem-loop and a method for preparing the same.

12 Claims, 6 Drawing Sheets

Specification includes a Sequence Listing.

SEQUENCE LISTING

<160> NUMBER OF SEQ ID NOS: 32

<210> SEQ ID NO 1
<211> LENGTH: 55
<212> TYPE: DNA
<213> ORGANISM: Artificial Sequence
<220> FEATURE:
<223> OTHER INFORMATION: Backbone sequence for double stem-loop

<400> SEQUENCE: 1
gaagctgacc agatcggtca gtttcccggg ccctcgcttc ggtgagggct ttacc    55

<210> SEQ ID NO 2
<211> LENGTH: 27
<212> TYPE: DNA
<213> ORGANISM: Artificial Sequence
<220> FEATURE:
<223> OTHER INFORMATION: Forward primer

<400> SEQUENCE: 2
gggatccata aatatgagcg gataaca    27

<210> SEQ ID NO 3
<211> LENGTH: 21
<212> TYPE: DNA
<213> ORGANISM: Artificial Sequence
<220> FEATURE:
<223> OTHER INFORMATION: Reverse primer

<400> SEQUENCE: 3
atctgtatca ggctgaaaat c    21

<210> SEQ ID NO 4
<211> LENGTH: 24
<212> TYPE: DNA
<213> ORGANISM: Artificial Sequence
<220> FEATURE:
<223> OTHER INFORMATION: Phenol_reg_01

<400> SEQUENCE: 4
aggcaagaaa aaagcaaaag ttct    24

<210> SEQ ID NO 5
<211> LENGTH: 22
<212> TYPE: DNA

```
<213> ORGANISM: Artificial Sequence
<220> FEATURE:
<223> OTHER INFORMATION: Phenol_reg_02

<400> SEQUENCE: 5
gatcggcagc aaaagtttgt gt                                            22

<210> SEQ ID NO 6
<211> LENGTH: 63
<212> TYPE: DNA
<213> ORGANISM: Artificial Sequence
<220> FEATURE:
<223> OTHER INFORMATION: Phenol_reg_03

<400> SEQUENCE: 6
tcccagacgt ttccagcggt tgacgatttc acaaaacagc acagcagtgc gttcggtgtc   60
gta                                                                 63

<210> SEQ ID NO 7
<211> LENGTH: 27
<212> TYPE: DNA
<213> ORGANISM: Artificial Sequence
<220> FEATURE:
<223> OTHER INFORMATION: Phenol_reg_04

<400> SEQUENCE: 7
gccatcaata aaatccagca ctcacat                                       27

<210> SEQ ID NO 8
<211> LENGTH: 25
<212> TYPE: DNA
<213> ORGANISM: Artificial Sequence
<220> FEATURE:
<223> OTHER INFORMATION: Phenol_reg_05

<400> SEQUENCE: 8
caacgaacca ccggttgcca ccacc                                         25

<210> SEQ ID NO 9
<211> LENGTH: 25
<212> TYPE: DNA
<213> ORGANISM: Artificial Sequence
<220> FEATURE:
<223> OTHER INFORMATION: Phenol_reg_06

<400> SEQUENCE: 9
gccaccggct accagcacag cacgg                                         25

<210> SEQ ID NO 10
<211> LENGTH: 28
<212> TYPE: DNA
<213> ORGANISM: Artificial Sequence
<220> FEATURE:
<223> OTHER INFORMATION: Phenol_reg_07

<400> SEQUENCE: 10
aaactaccag caaaacataa atccccac                                      28

<210> SEQ ID NO 11
<211> LENGTH: 30
<212> TYPE: DNA
<213> ORGANISM: Artificial Sequence
<220> FEATURE:
<223> OTHER INFORMATION: Phenol_reg_08

<400> SEQUENCE: 11
```
accgcttccc ttaataggtc cgcacgagga                                30

<210> SEQ ID NO 12
<211> LENGTH: 59
<212> TYPE: DNA
<213> ORGANISM: Artificial Sequence
<220> FEATURE:
<223> OTHER INFORMATION: Phenol_reg_09

<400> SEQUENCE: 12
ttttacccag cccaacaatc tccccacata tcccgctatc attaccgttt tcctccagc   59

<210> SEQ ID NO 13
<211> LENGTH: 38
<212> TYPE: DNA
<213> ORGANISM: Artificial Sequence
<220> FEATURE:
<223> OTHER INFORMATION: cinnamic aldehyde_reg_01

<400> SEQUENCE: 13
aatcagcggt ttttgtggaa tggcaaggtt gttagata                       38

<210> SEQ ID NO 14
<211> LENGTH: 105
<212> TYPE: DNA
<213> ORGANISM: Artificial Sequence
<220> FEATURE:
<223> OTHER INFORMATION: cinnamic aldehyde_reg_02

<400> SEQUENCE: 14
tgtttgaccg cccctgtttt ttagcgtcag gcatgatgcc ctccaatatg gttattttt   60 attgtgaatt aagataggtg agtacgacgt aaaaagatgt gaagc                 105

<210> SEQ ID NO 15
<211> LENGTH: 180
<212> TYPE: DNA
<213> ORGANISM: Artificial Sequence
<220> FEATURE:
<223> OTHER INFORMATION: cinnamic aldehyde_reg_03

<400> SEQUENCE: 15
acagtttcgc ttggtggttt ctcaactcat agcgagagta tcggatattt tacatgccga  60
caacttcgcc atcaagcagc gccagatggt agcgcatgtt tgggtcgcgc agattggcgt   120
taaaacccac gcgaaacgcg tggtggtcaa actccgcctg ttttagctca caaatcagcg   180

<210> SEQ ID NO 16
<211> LENGTH: 48
<212> TYPE: DNA
<213> ORGANISM: Artificial Sequence
<220> FEATURE:
<223> OTHER INFORMATION: cinnamic aldehyde_reg_04

<400> SEQUENCE: 16
tgagcagtga ttttcagctt atcgccggaa cggtgcgcga tttgcgcc             48

<210> SEQ ID NO 17
<211> LENGTH: 79
<212> TYPE: DNA
<213> ORGANISM: Artificial Sequence
<220> FEATURE:
<223> OTHER INFORMATION: cinnamic aldehyde_reg_05

<400> SEQUENCE: 17

```
tattcattgc ttctacccgt gcctcgcttt ctgtattacg aaattgtccc aacacatgtg    60
ccagccgata aaacccac                                                  79

<210> SEQ ID NO 18
<211> LENGTH: 157
<212> TYPE: DNA
<213> ORGANISM: Artificial Sequence
<220> FEATURE:
<223> OTHER INFORMATION: cinnamic aldehyde_reg_06

<400> SEQUENCE: 18
aacgcagggc gttcgaaagc aggttgctta gcgcccgacg cagcatcagc ggatcgcccg    60
cgacctgaca cttgtcgcca acaaaccgca actccacgcc gcgatcttcc gctaacgcct  120
cgaaaaaatc gaacactttg ccgacttcat ccgccag                            157

<210> SEQ ID NO 19
<211> LENGTH: 33
<212> TYPE: DNA
<213> ORGANISM: Artificial Sequence
<220> FEATURE:
<223> OTHER INFORMATION: cinnamic aldehyde_reg_07

<400> SEQUENCE: 19
aatccctcaa tgatgcctgg aatcgctctt tta                                 33

<210> SEQ ID NO 20
<211> LENGTH: 48
<212> TYPE: DNA
<213> ORGANISM: Artificial Sequence
<220> FEATURE:
<223> OTHER INFORMATION: cinnamic aldehyde_reg_08

<400> SEQUENCE: 20
ggcgctgcat ccgcgttata gccgcgccca gtatgaccgg gtaatgga                 48

<210> SEQ ID NO 21
<211> LENGTH: 41
<212> TYPE: DNA
<213> ORGANISM: Artificial Sequence
<220> FEATURE:
<223> OTHER INFORMATION: cinnamic aldehyde_reg_09

<400> SEQUENCE: 21
tccaccattt cggagagttt tttacgcgcc agcgggcggc t                        41

<210> SEQ ID NO 22
<211> LENGTH: 71
<212> TYPE: DNA
<213> ORGANISM: Artificial Sequence
<220> FEATURE:
<223> OTHER INFORMATION: cinnamic aldehyde_reg_10

<400> SEQUENCE: 22
attactgcgc cagttgaggc cctgggtttt gaactggttg gcatcgaatt tattcgcggt    60
cgcacatcca c                                                         71

<210> SEQ ID NO 23
<211> LENGTH: 73
<212> TYPE: DNA
<213> ORGANISM: Artificial Sequence
<220> FEATURE:
<223> OTHER INFORMATION: cinnamic aldehyde_reg_11

<400> SEQUENCE: 23
```

```
cccttcgcca acaatcccgg agagcgccac agcatcggtc ggagaaagca ccgccgccag    60
cgcaaaggca ggg                                                       73
```

<210> SEQ ID NO 24
<211> LENGTH: 24
<212> TYPE: DNA
<213> ORGANISM: Artificial Sequence
<220> FEATURE:
<223> OTHER INFORMATION: cinnamic aldehyde_reg_12

<400> SEQUENCE: 24

```
gggcaagggc aaacatttgc gggt                                           24
```

<210> SEQ ID NO 25
<211> LENGTH: 40
<212> TYPE: DNA
<213> ORGANISM: Artificial Sequence
<220> FEATURE:
<223> OTHER INFORMATION: cinnamic aldehyde_reg_13

<400> SEQUENCE: 25

```
accgtcataa cgcggcttct cacctttcgc catttgctct                          40
```

<210> SEQ ID NO 26
<211> LENGTH: 18
<212> TYPE: DNA
<213> ORGANISM: Artificial Sequence
<220> FEATURE:
<223> OTHER INFORMATION: cinnamic aldehyde_reg_14

<400> SEQUENCE: 26

```
cccacggtga cgggcatt                                                  18
```

<210> SEQ ID NO 27
<211> LENGTH: 113
<212> TYPE: DNA
<213> ORGANISM: Artificial Sequence
<220> FEATURE:
<223> OTHER INFORMATION: cinnamic aldehyde_reg_15

<400> SEQUENCE: 27

```
aacaaaatat tccgcgcgct gtgcggccca cttggcggca taatcaccac ctacagcaaa    60
gtgaaatccc ctacccgcgt gatccaaatc ctttccgtac tcggcctgct gac          113
```

<210> SEQ ID NO 28
<211> LENGTH: 113
<212> TYPE: DNA
<213> ORGANISM: Artificial Sequence
<220> FEATURE:
<223> OTHER INFORMATION: cinnamic aldehyde_reg_16

<400> SEQUENCE: 28

```
aacaaaatat tccgcgcgct gtgcggccca cttggcggca taatcaccac ctacagcaaa    60
gtgaaatccc ctacccgcgt gatccaaatc ctttccgtac tcggcctgct gac          113
```

<210> SEQ ID NO 29
<211> LENGTH: 58
<212> TYPE: DNA
<213> ORGANISM: Artificial Sequence
<220> FEATURE:
<223> OTHER INFORMATION: cinnamic aldehyde_reg_17

<400> SEQUENCE: 29

```
cccctccggca gttggaagtt tttgcagaag tattgaaaag tggatcaacc acccaggc      58
```

<210> SEQ ID NO 30
<211> LENGTH: 94
<212> TYPE: DNA
<213> ORGANISM: Artificial Sequence
<220> FEATURE:
<223> OTHER INFORMATION: cinnamic aldehyde_reg_18

<400> SEQUENCE: 30

```
ctccatctta ttccatcagg tattctccgc gagaatgtaa ccagcatcat cggtaacggt      60
gttgtgctgt ctccggccgc gctgatgaaa gaga                                  94
```

<210> SEQ ID NO 31
<211> LENGTH: 56
<212> TYPE: DNA
<213> ORGANISM: Artificial Sequence
<220> FEATURE:
<223> OTHER INFORMATION: cinnamic aldehyde_reg_19

<400> SEQUENCE: 31

```
ccgggaattc aaaacctcgc ggcaaaccat tttaagagcc aaagcaaaac ttcaga          56
```

<210> SEQ ID NO 32
<211> LENGTH: 4269
<212> TYPE: DNA
<213> ORGANISM: Artificial Sequence
<220> FEATURE:
<223> OTHER INFORMATION: pHM4T-dSL-SmaI plasmid

<400> SEQUENCE: 32

```
ttgacattgt gagcggataa caatataatg aattccgaag ctgaccagat cggtcagttt      60
cccgggccct cgcttcggtg agggctttac caagcttttg gctgttttgg cggatgagag     120
aagattttca gcctgataca gattaaatca gaacgcagaa gcggtctgat aaaacagaat     180
ttgcctggcg gcagtagcgc ggtggtccca cctgacccca tgccgaactc agaagtgaaa     240
cgccgtagcg ccgatggtag tgtggggtct ccccatgcga gagtagggaa ctgccaggca     300
tcaaataaaa cgaaaggctc agtcgaaaga ctgggccttt cgttttatct gttgtttgtc     360
ggtgaacgct ctcctgagta ggacaaatcc gccgggagcg gatttgaacg ttgcgaagca     420
acggcccgga gggtggcggg caggacgccc gccataaact gccaggcatc aaattaagca     480
gaaggccatc ctgacggatg gcctttttgc gtttctacaa actcttttgt ttatttttct     540
aaatacattc aaatatgtat ccgctcatga gacaataacc ctgataaatg cttcaataat     600
attgaaaaag gaagagtatg agtattcaac atttccgtgt cgcccttatt ccctttttttg     660 cggcattttg ccttcctgtt tttgctcacc cagaaacgct ggtgaaagta aaagatgctg     720
aagatcagtt gggtgcacga gtgggttaca tcgaactgga tctcaacagc ggtaagatcc     780
ttgagagttt tcgccccgaa gaacgttttc caatgatgag cacttttaaa gttctgctat     840
gtggcgcggt attatcccgt gttgacgccg ggcaagagca actcggtcgc cgcatacact     900
attctcagaa tgacttggtt gagtactcac cagtcacaga aaagcatctt acggatggca     960
tgacagtaag agaattatgc agtgctgcca taaccatgtg tgataacact gcggccaact    1020
tacttctgac aacgatcgga ggaccgaagg agctaaccgc ttttttgcac aacatggggg    1080
atcatgtaac tcgccttgat cgttgggaac cggagctgaa tgaagccata ccaaacgacg    1140
agcgtgacac cacgatgctg tagcaatggc aacaacgttg cgcaaactat taactggcga    1200
actacttact ctagcttccc ggcaacaatt aatagactgg atggaggcgg ataaagttgc    1260
```

```
aggaccactt ctgcgctcgg cccttccggc tggctggttt attgctgata aatctggagc   1320
cggtgagcgt gggtctcgcg gtatcattgc agcactgggg ccagatggta agccctcccg   1380
tatcgtagtt atctacacga cggggagtca ggcaactatg gatgaacgaa atagacagat   1440
cgctgagata ggtgcctcac tgattaagca ttggtaactg tcagaccaag tttactcata   1500
tatactttag attgatttaa aacttcattt ttaatttaaa aggatctagg tgaagatcct   1560
ttttgataat ctcatgacca aaatccctta acgtgagttt tcgttccact gagcgtcaga   1620
ccccgtagaa aagatcaaag gatcttcttg agatcctttt tttctgcgcg taatctgctg   1680
cttgcaaaca aaaaaaccac cgctaccagc ggtggtttgt ttgccggatc aagagctacc   1740 aactctttt ccgaaggtaa ctggcttcag cagagcgcag ataccaaata ctgtccttct   1800
agtgtagccg tagttaggcc accacttcaa gaactctgta gcaccgccta catacctcgc   1860
tctgctaatc ctgttaccag tggctgctgc cagtggcgat aagtcgtgtc ttaccgggtt   1920
ggactcaaga cgatagttac cggataaggc gcagcggtcg ggctgaacgg ggggttcgtg   1980
cacacagccc agcttggagc gaacgaccta caccgaactg agatacctac agcgtgagca   2040
ttgagaaagc gccacgcttc ccgaagggag aaaggcggac aggtatccgg taagcggcag   2100
ggtcggaaca ggagagcgca cgagggagct tccagggga aacgcctggt atctttatag   2160
tcctgtcggg tttcgccacc tctgacttga gcgtcgattt ttgtgatgct cgtcaggggg   2220
gcggagccta tggaaaaacg ccagcaacgc ggcctttta cggttcctgg ccttttgctg   2280
gccttttgct cacatgttct ttcctgcgtt atccctgat tctgtggata accgtattac   2340
cgcctttgag tgagctgata ccgctcgccg cagccgaacg accgagcgca gcgagtcagt   2400
gagcgaggaa gcggaagagc gcctgatgcg gtattttctc cttacgcatc tgtgcggtat   2460
ttcacaccgc atatgaggac accatcgaat ggtgcaaaac ctttcgcggt atggcatgat   2520
agcgcccgga agagagtcaa ttcagggtgg gtgaatggtg aaaccagtaa cgttatacga   2580
tgtcgcagag tatgccggtg tctcttatca gaccgtttcc cgcgtggtga accaggccag   2640
ccacgtttct gcgaaaacgc gggaaaaagt ggaagcggcg atggcggagc tgaattacat   2700
tcccaaccgc gtggcacaac aactggcggg caaacagtcg ttgctgattg gcgttgccac   2760
ctccagtctg gccctgcacg cgccgtcgca aattgtcgcg gcgattaaat ctcgcgccga   2820
tcaactgggt gccagcgtgg tggtgtcgat ggtagaacga agcggcgtcg aagcctgtaa   2880
agcggcggtg cacaatcttc tcgcgcaacg cgtcagtggg ctgatcatta actatccgct   2940
ggatgaccag gatgccattg ctgtggaagc tgcctgcact aatgttccgg cgttatttct   3000
tgatgtctct gaccagacac ccatcaacag tattattttc tcccatgaag acggtacgcg   3060
actgggcgtg gagcatctgg tcgcattggg tcaccagcaa atcgcgctgt tagcgggccc   3120
attaagttct gtctcggcgc gtctgcgtct ggctggctgg cataaatatc tcactcgcaa   3180
tcaaattcag ccgatagcgg aacgggaagg cgactgagt gccatgtccg gttttcaaca   3240
aaccatgcaa atgctgaatg agggcatcgt tcccactgcg atgctggttg ccaacgatca   3300
gatggcgctg ggcgcaatgc gcgccattac cgagtccggg ctgcgcgttg gtgcggatat   3360
ctcggtagtg ggatacgacg ataccgaaga cagctcatgt tatatcccgc cgttaaccac   3420
catcaaacag gattttcgcc tgctggggca accagcgtg gaccgcttgc tgcaactctc   3480
tcagggccag gcggtgaagg gcaatcagct gttgcccgtc tcactggtga aaagaaaaac   3540
caccctggcg cccaatacgc aaaccgcctc tccccgcgcg ttggccgatt cattaatgca   3600
```

```
                                                                        -continued
gctggcacga caggtttccc gactggaaag cgggcagtga gcgcaacgca attaatgtaa        3660
gttagctcac tcattaggca ccccaggctt tacactttat gcttccggct cgtataatgt        3720
gtggaattgt gagcggataa caatttcaca caggaaacag ctatgaccat gattacggat        3780
tcactggccg tcgttctcga gctgcttgag ccagtgagcg attgctggcc tagatgaatg        3840
actgtccacg acagaacccg gcttatcggt cagtttcacc tgatttacgt aaaaacccgc        3900
ttcggcgggt ttttgctttt ggaggggcag aaagatgaat gactgtccac gacgctatac        3960
ccaaaagaaa gcggcttatc ggtcagtttc acctggttta cgtaaaaacc cgcttcggcg        4020 ggttttttgct tttggagggg cagaaagatg aatgactgtc cacgacacta tacccaaaag       4080
aaagcggctt atcggtcagt ttcacctgtt ttacgtaaaa acccgcttcg gcgggttttt        4140
acttttggag gggcagaaag atgaatgact gtccacgaca ctatacccaa aagaaagcgg        4200
cttatcggtc agttttacct gatgtacgta ataaaccgtt ccgggatcca taaatatgag        4260
cggataaca                                                                4269
```

GENOME-ORIGINATED ARTIFICIAL NCRNA EXPRESSION LIBRARY AND METHOD OF PREPARING THE SAME

CROSS-REFERENCE TO RELATED APPLICATION

This application claims priority under 35 U.S.C. § 119 to Korean Patent Application No. 10-2016-0102606, filed in the Korean Intellectual Property Office on Aug. 11, 2016, the disclosure of which is incorporated by reference herein in its entirety.

BACKGROUND OF THE INVENTION

(a) Field of the Invention

The present invention relates to an artificial ncRNA expression library and a method for preparing the same, and particularly the present invention relates to a library securing the stability of the artificial ncRNA by cloning random fragmented DNA that whole genome DNA of *E. coli* is randomly fragmented to a middle of RNA scaffold having a double stem-loop and a method for preparing the same.

(b) Description of the Related Art

In many research fields of biology, a method for finding a specific gene using gene screening is a very common and well-known method. Such gene screening is, a method of sorting genes which affect cell metabolism under a specific condition using a wide range of gene library.

The gene library can be roughly divided into genomic DNA library obtained by cutting genomic DNA into an appropriate size and cloning it to a plasmid or a phage vector and cDNA library obtained by cloning cDNA for mRNA to a plasmid or a phage vector. These two libraries are basically designed to be used to screen genes encoding proteins.

However recently it has been found that non-coding RNA (ncRNA), not proteins actively act on cell metabolism. Therefore if ncRNA expression library is present, ncRNA which affects cell metabolism under a specific condition can be screened. In particular, ncRNA library has an advantage in that both increase and reduction of gene expression are based on screening, while a gene expression increase effect is based on screening for the genome DNA library and the ncRNA library.

Such ncRNA exists in all kinds of cells, and researches on ncNRA like a research of gene expression control by miRNA and its utilizing method have been remarkably paid attention as RNA interference was revealed in eukaryote. 50 to 400 nucleotides (nt) of various ncRNAs exist in bacteria (Gisela Storz et al., 2011, Mol Cell, 43(6):880-91). In *E. coli*, up to now, there are approximately 100 kinds of ncRNAs that actual expression has been experimentally identified (Gisela Storz et al., 2011, Mol Cell, 43(6):880-91), but intracellular function of a part among them has been discovered and functions of a considerable number of ncRNA are not discovered yet. In addition, in case of ncRNA that its function was discovered, new functions have been discovered.

In most cases, bacterial ncRNAs control stability of mRNA by making a base pair with a specific part of mRNAs which are targeted and control cell metabolic processes by inhibiting a translation process. Besides there are ncRNAs which directly combine to a global transcription control protein, thereby controlling its function, or work as decoy of RNA being decomposed, or work in order to decompose a phage or an external plasmid DNA (Gisela Storz et al., 2011, Mol Cell, 43(6):880-91).

Recently the development of an artificial ncRNA capable of mimicking the function of natural ncRNA in *E. coli* has been attempted, and an artificial ncRNA can be widely applied to gene expression control in a molecular biology field and to cell activity control by metabolic engineering in a synthetic biology field.

However, there are a lot of problems in the development of an artificial ncRNA causing desirable control pattern or cell phenotype so far. That is because it is difficult to design an artificial ncRNA as an acting pattern of an artificial ncRNA is too complex. A method for screening desirable artificial ncRNA by constructing random nucleotide sequence library to solve the problems has been developed, but there are two problems in random nucleotide sequence library. One is to make random nucleotide sequence have stability in a cell, and the other is that it is impossible to actually construct library, if the number of random nucleotide sequences increases.

SUMMARY OF THE INVENTION

Hence, the object of the present invention is to provide a method for preparing a genome-originated artificial ncRNA library.

Another object of the present invention is to provide a genome-originated artificial ncRNA library.

Another object of the present invention relates to a use of the genome-originated artificial ncRNA library.

The present inventors have successfully constructed an artificial ncRNA expression library that securing the stability in a cell of the artificial ncRNA by cloning nucleotide sequences of random fragmented DNA that whole genome DNA of *E. coli* is randomly fragmented in lengths of average 50 nucleotides (nt) instead of random nucleotide sequences to a middle of RNA scaffold having a double stem-loop in order to overcome the problems.

Accordingly the constructed library is named as *E. coli* genome-originated artificial ncRNA expression library (GOAL).

Hereinafter, the present invention will be described in greater detail.

One embodiment of the present invention relates to a method for preparing an artificial ncRNA expression library comprising the following steps:

1) preparing a random fragmented DNA that randomly fragments whole genome DNA;

2) making a terminal end of the random fragmented DNA a blunt end;

3) preparing an artificial ncRNA expression plasmid by connecting the DNA fragment with the blunt end to a plasmid DNA;

4) transforming a cell by the artificial ncRNA expression plasmid; and 5) constructing an artificial ncRNA expression library by purifying the artificial ncRNA expression plasmid from the transformed cell:

wherein the whole genome can be a whole genome of pKoreaaryote, for example, a whole genome of *escherichia coli, Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhizobium, Rhodobacter, Zymomonas, Bacillus, Staphylococcus, Lactococcus, Streptococcus, Lactobacillus,*

*Clostridium, Corynebacterium, Streptomyces, Bifidobacterium,* or *Cyclobacterium,* and preferably it can be a whole genome of *Escherichia coli*. In addition, the whole genome of *Escherichia coli* can be *E. coli* genome DNA extracted from a cell.

Furthermore, the plasmid DNA can be prepared by steps comprising:
a step of treating a restriction enzyme to a plasmid; and
a step of treating phosphatase, but not limited thereto.

The plasmid DNA is that the terminal is dephosphorylated.

The treatment of phosphatase is dephosphorylation using Antarctic phosphatase, in order to prevent self-coupling in a step of connecting DNA fragments to the plasmid after fragmentation by treating a restriction enzyme to the plasmid.

The plasmid DNA can comprise nucleotide sequences encoding a double stem-loop type of RNA scaffold. For example, the RNA scaffold can comprise a double stem-loop type of SibC terminator hairpin and P1 stem-loop of M1 RNA, but not limited thereto.

A restriction site can be comprised in the nucleotide sequences encoding the RNA scaffold.

The restriction enzyme site can be a site where an enzyme producing a blunt end recognizes, and for example, the enzyme producing a blunt end can be AanI, Acc16I, AccBSI, AccII, AcvI, AfaI, AfeI, AhaIII, AjiI, AleI, AluBI, AluI, Aor51HI, Asp700I, BalI, BbrPI, BmcAI, BmgBI, BmiI, BoxI, BsaAI, BsaBI, Bse8I, BseII, Bsh1236I, BshFI, BsnI, Bsp68I, BspANI, BspFNI, BspLI, BsrBI, BssNAI, Bst1107I, BstBAI, BstC8I, BstFNI, BstPAI, BstSNI, BstUI, BstZ17I, BsuRI, BtrI, BtuMI, Cac8I, CdiI, CviJI, CviKI 1, CviRI, DinI, DpnI, DraI, Ec1136II, Eco105I, Eco147I, Eco32I, Eco47III, Eco53kI, Eco72I, EcoICRI, EcoRV, EgeI, EheI, EsaBC3I, FaiI, FnuDII, FspAI, FspI, GlaI, HaeI, HaeIII, HincII, HindII, HpaI, Hpyl66II, Hpy8I, HpyCH4V, KspAI, LpnI, MalI, MbiI, MlsI, MluNI, MlyI, Mox20I, MroXI, MscI, Ms1I, Msp20I, MspA1I, MssI, MstI, MvnI, NaeI, NgoAVII, NlaIV, NruI, NsbI, NspBII, OliI, PceI, PdiI, PdmI, PmaCI, PmeI, Pm1I, Ppu21I, PshAI, PsiI, PspCI, PspN4I, PvuII, RruI, RsaI, RseI, ScaI, SchI, SciI, SfoI, SmaI, SmiI, SmiMI, SnaBI, SrfI, SseBI, SspD5I, SspI, Sth302II, StuI, SwaI, XmnI, ZraI or ZrmI, and preferably it can be SmaI that wasted nucleotide sequences which can work on non-specific reactions are little, since an enzyme recognition site is short and 2 nucleotide sequences of the enzyme recognition site is included in scaffold of the double stem-loop.

The nucleotide sequences encoding the double stem-loop type of RNA scaffold can comprise the nucleotide sequence of SEQ ID NO: 1, and for example, it can comprise the nucleotide sequence of SEQ ID NO: 32.

SEQ ID NO: 1:
5'-GAAGCTGACCAGATCGGTCAGTTTCCCGGGCCCTCGCTTCGGTGAG
GGCTTTACC-3'

The part of $25^{th}$ to $30^{th}$ bases of the SEQ ID NO: 1 is the nucleotide sequence that a restriction enzyme recognizes, and a random fragmented DNA is inserted by fragmenting an area between the $27^{th}$ base and the $28^{th}$ base by the restriction enzyme.

Since such double stem-loop RNA scaffold can provide stability to an artificial ncRNA and genome-originated DNA fragments are sources of supply of random RNA nucleotide sequences, the artificial ncRNA constructed by the method is more effective because potentially antisense RNA to all genes can be comprised, and the number of clones that should be constructed as a random library can be innovatively reduced.

The plasmid DNA can be a plasmid DNA where RNA expression occurs well as producing unnecessary RNA little that is generated by not good transcription termination, and having a strong promoter.

The whole genome DNA can fragment using DNase I.

A random fragmentation of the whole genome DNA, can control a length of random fragmented DNA as 10 to 100 bases, 20 to 100 bases, 30 to 100 bases, 40 to 100 bases, 10 to 90 bases, 20 to 90 bases, 30 to 90 bases, 40 to 90 bases, 10 to 80 bases, 20 to 80 bases, 30 to 80 bases, 40 to 80 bases, 10 to 70 bases, 20 to 70 bases, 30 to 70 bases, 40 to 70 bases, 10 to 60 bases, 20 to 60 bases, 30 to 60 bases, or 40 to 60 bases, for example 50 bases by controlling concentration of manganese ions, and time and temperature of treating DNase. In case that the length of random fragmented DNA corresponds to the range, effects of easy screening and enhanced reaction accuracy of RNA are obtained, since if the length of random fragmented DNA is shorter, a problem that screening is difficult occurs as requiring more plasmids, and if that is longer than the range, a problem that reaction accuracy of RNA is reduced.

The concentration of manganese ions can be 5 to 15 mM, 5 to 14 mM, 5 to 13 mM, 5 to 12 mM, 5 to 11 mM, 6 to 15 mM, 6 to 14 mM, 6 to 13 mM, 6 to 12 mM, 6 to 11 mM, 7 to 15 mM, 7 to 14 mM, 7 to 13 mM, 7 to 12 mM, 7 to 11 mM, 8 to 15 mM, 8 to 14 mM, 8 to 13 mM, 8 to 12 mM, 8 to 11 mM, 9 to 15 mM, 9 to 14 mM, 9 to 13 mM, 9 to 12 mM, 9 to 11 mM, for example, 10 mM. In case of conducting in the concentration range of manganese ions, when DNA cuts DNA, a significant effect to minimize single strand parts and cut in a double strand type is obtained.

The treatment of DNase can be conducted at 15 to 25° C., 16 to 25° C., 17 to 25° C., 18 to 25° C., 19 to 25° C., 15 to 24° C., 16 to 24° C., 17 to 24° C., 18 to 24° C., 19 to 24° C., 15 to 23° C., 16 to 23° C., 17 to 23° C., 18 to 23° C., 19 to 23° C., 15 to 22° C., 16 to 22° C., 17 to 22° C., 18 to 22° C., 19 to 22° C., 15 to 21° C., 16 to 21° C., 17 to 21° C., 18 to 21° C., 19 to 21° C., for example, 20° C.

The time conducting the treatment of DNase can be for 5 to 7 min, preferably for 6 min.

In case of conducting the treatment of DNase at the temperature and the time, a significant effect to obtain double strand that the average length of random fragmented DNA is approximately 50 nt is obtained.

The step of making a random fragmented DNA terminal a blunt end can be preparing in the way of decomposing 3' overhang of the random fragmented DNA and filling 5' overhang.

The step of making a random fragmented DNA terminal a blunt end can be conducted by using T4 DNA polymerase, but not limited thereto.

The T4 DNA polymerase makes random fragmented DNA terminal a blunt end by decomposing 3' overhang of random fragmented DNA in case of absence of dNTP, and filling lacking part of 5' overhang of random fragmented DNA through polymerization using dNTP in case of presence of dNTP.

The step of making a random fragmented DNA terminal a blunt end can be filling 5' overhang by adding only dNTP without replacing reaction solution after decomposing 3' overhang. In case of conducting the step without replacing reaction solution, there is an effect to proceed a response effectively, since new purification is not needed and it is not needed to change the composition of buffer solution.

After the step of constructing an artificial ncRNA expression library, a step of verifying library construction can be further conducted by conducting colony PCR reaction, but not limited thereto. Since a case that DNA fragments are not inserted to RNA scaffold and attach again occurs, and in case that its ratio is high, it is difficult to proceed screening as many plasmids are thrown away when collecting 300,000 colonies, the step of verifying is a step of confirming that the ratio of plasmids that DNA fragments are inserted is high by verifying it.

The PCR reaction can be conducted by using the primer pair consisting of nucleotide sequences of SEQ ID NO: 2 and SEQ ID NO: 3.

```
SEQ ID NO: 2:
5'-GGG ATC CAT AAA TAT GAG CGG ATA ACA-3'

SEQ ID NO: 3:
5'-ATC TGT ATC AGG CTG AAA ATC-3'
```

The verification can be conducted by investigating a size of an artificial ncRNA.

The verification can be confirming a size of random fragmented DNA through checking nucleotide sequences after colony PCR reaction.

The random fragmented DNA can consist of 10 to 100 bases, 20 to 100 bases, 30 to 100 bases, 40 to 100 bases, 10 to 90 bases, 20 to 90 bases, 30 to 90 bases, 40 to 90 bases, 10 to 80 bases, 20 to 80 bases, 30 to 80 bases, 40 to 80 bases, 10 to 70 bases, 20 to 70 bases, 30 to 70 bases, 40 to 70 bases, 10 to 60 bases, 20 to 60 bases, 30 to 60 bases, or 40 to 60 bases, for example 50 bases.

Another embodiment of the present invention relates to an artificial ncRNA expression library prepared by the method for preparing an artificial ncRNA expression library.

Another embodiment of the present invention relates to a method for screening an artificial ncRNA, which is to improve resistance to stress in a cell using the artificial ncRNA expression library prepared as above.

The artificial ncRNA prepared by the artificial ncRNA expression library has a feature of controlling expression of genes that natural ncRNA in *E. coli* cannot target, and screening such artificial ncRNA means a process to find an artificial ncNRA which improves resistance to stress using the feature and to find what is the gene that the artificial ncRNA targets.

The resistance to stress can mean resistance to harmful compounds, temperature, acidity, salinity, etc., but not limited thereto, and can be any stress condition that an experimenter wants.

In other words, since the artificial ncRNA expression library of the present invention can express all the artificial ncRNA which can control expression of any gene in a cell, because of this, an artificial ncRNA causing desirable control patterns or a cell phenotype can be screened.

Thus the present inventors have screened an artificial ncRNA which can improve resistance to phenol or resistance to cinnamaldehyde in *E. coli* by utilizing the artificial ncRNA expression library.

Another embodiment of the present invention relates to an artificial ncRNA for improving resistance to phenol comprising a nucleotide sequence selected from the group consisting of SEQ ID NOs: 4 to 12.

Another embodiment of the present invention relates to a composition for improving resistance to phenol comprising an artificial ncRNA comprising a nucleotide sequence selected from the group consisting of SEQ ID NOs: 4 to 12.

Another embodiment of the present invention relates to an artificial ncRNA for improving resistance to cinnamaldeyde comprising a nucleotide sequence selected from the group consisting of SEQ ID NOs: 13 to 31.

Another embodiment of the present invention relates to a composition for improving resistance to cinnamaldeyde comprising an artificial ncRNA comprising a nucleotide sequence selected from the group consisting of SEQ ID NOs: 13 to 31.

As such the artificial ncRNA expression library of the present invention can be used for screening an artificial ncRNA which can improve productivity of a strain producing useful substances by controlling various metabolisms of cell.

In addition, it can be utilized to not only academic researches related to metabolic regulation of a target gene or a target biomolecule but also application researches like cell metabolism engineering, as it can identify a target gene or a target biomolecule of an artificial ncRNA, and identified target gene or target biomolecule can be used to control a specific metabolism of *E. coli* or to apply to cell metabolism engineering, as a target gene or a target biomolecule of an artificial ncRNA can be identified.

The present invention relates to an artificial ncRNA expression library and a method for preparing the same, and particularly the present invention relates to a library securing the stability of the artificial ncRNA by cloning random fragmented DNA that whole genome DNA of *E. coli* is randomly fragmented to a middle of RNA scaffold having a double stem-loop and a method for preparing the same.

DETAILED DESCRIPTION OF THE EMBODIMENTS

Figure 1:
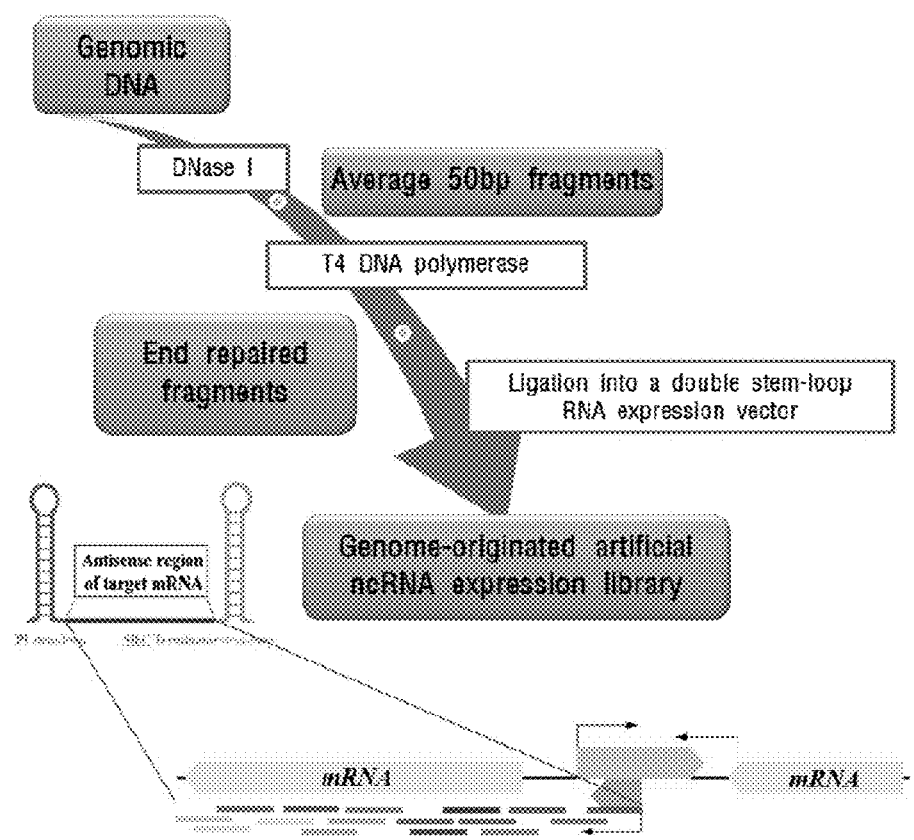
FIG. 1 is a diagram of the method for constructing a genome-originated artificial ncRNA library (GOAL) according to one example of the present invention.

Hereinafter, the present invention will be described in more detail by the following examples. However, these examples are provided only for illustration, and the scope of the present invention is not limited by these examples.

Example 1. Treatment of a Restriction Enzyme and Phosphatase of an Artificial ncRNA Expression Vector pHM4T-dSL-SmaI plasmid consisting of SEQ ID NO: 32 was obtained from DH5a E. coli cell (Bak G et al., Methods Mol Biol, 1316, 211-225), and 3 µg of obtained plasmid DNA was cut using a 10-fold excess of SmaI restriction enzyme (Promega, USA, R6121).

Then, total 100 µL of reaction solution was prepared by mixing the cut plasmid 50 µL (~3 µg), 10× restriction enzyme reaction buffer solution (Promega, USA, R6121) 10 uL, distilled water (Nuclease-freewater, NFW) 37 µL, and SmaI restriction enzyme (Promega, USA, R6121) 3 µL (30 U), and after reacted at 25° C. for 4 to 6 hrs, the restriction enzyme was inactivated by transferring to 65° C. and reacting for 20 mins.

Then, 10× Antarctic phosphatase reaction buffer solution (New England BioLabs, UK) 10 µL and Antarctic phosphatase (New England BioLabs, UK, M0289) 1 µL were added to the reaction solution that the restriction enzyme was inactivated, and after reacted in a 37° C. constant-temperature water bath for 25 mins, the phosphatase was inactivated by heating at 65° C. for 10 mins.

Then, electrophoresis of the reaction solution that the phosphatase was inactivated was done in 1% agarose gel, and 4268 bp of dephosphorylated DNA band was cut from the gel, thereby purifying DNA using spin-column type of gel extraction kit (Intron Biotechnology, KOREA, 17288), and after dissolving in 30 to 50 uL distilled water, purity and amount of DNA was measured using Nanodrop (Thermo Scientific, USA). As a result, it was demonstrated that the purity was approximately 2.0 as an OD260/OD280 value, and the concentration of phosphorylated linear DNA was over 30 ng/µL.

Example 2. Preparation of DNA Fragments Randomly Cutting Whole Genome DNA 2-1. Purification of Total DNA of E. coli Total DNA was extracted and purified using spin-column type of E. coli total DNA extraction kit (Intron Biotechnology, KOREA, 17046) from E. coli (MG1655, origin: CGSC6300. ATCC47076), and its purity and amount was measured using Nanodrop (Thermo Scientific, USA). As a result, it was demonstrated that the purity was approximately 2.0 as an OD260/OD280 value, and the concentration was over 1 µg/µL.

2-2. Random Fragmentation Using DNase I

In order to fragment total DNA of E. coli which was extracted and purified in Example 2-1, a solution having the composition as the following table 1 was prepared in total 3 of 1.5 ml centrifuge tubes in ice.

TABLE 1

| Genomic DNA | 20 ul (12 ug) |
|---|---|
| Tris-HCl, pH 7.4, 1M | 3 ul (50 mM) |
| MnCl2 200 mM | 3 ul (10 mM) |
| 1 mg/ml BSA | 5 ul (50 ug/ml) |
| DNase I | 2 ul (2 unit) |
| NFW (distilled water) | 27 ul |
| Total | 60 ul |

Then, prepared centrifuge tubes were reacted at 20° C. for 7 minutes, and phenol/chloroform (for DNA) 500 ul was added, thereby stopping reaction. Then, after adding 500 ul nuclease-free water to centrifuge tubes and voltexing for 30 secs, the supernatant was removed by centrifuging for 5 mins at 10000 g at a room temperature, and after adding chloroform as the same volume with removed supernatant and voltexing for 30 secs, the supernatant was removed again by centrifuging for 5 mins at 10000 g at a room temperature. Then, 3M NaOAC solution (pH 5.5) was added as much as 1/10 volume of DNA solution. Next, after adding 100% ethanol as much as 2.5 volumes and voltexing, it was stored at −70° C. for 16 hrs.

Then, the solution was taken out on ice and centrifuged for 5 minutes at 10000 g, thereby removing supernatant to leave only the precipitate, and after adding 70% ethanol 1 ml and washing centrifuge tubes, the supernatant was removed by centrifuging for 5 mins at 4° C. at 10000 g. After adding 100% ethanol 1 ml and washing centrifuge tubes again, it was centrifuged for 5 mins at 4° C. at 10000 g, and the supernatant was removed. Then, after drying precipitate for 10 mins in Speed Vac (Jeio Tech), all the 3 centrifuge tubes were mixed and dissolved in distilled water, and the purity and amount of DNA was measured using Nanodrop (Thermo Scientific, USA). As a result, it was demonstrated that the purity was approximately 2.0 as an OD260/OD280 value, and the concentration of phosphorylated linear DNA was over 100 ng/µL.

2-3. Formation of a Blunt End

In order to make the end of fragmented DNA a blunt end, a solution having the composition as the following table 2 was prepared in 1.5 ml centrifuge tubes on ice.

TABLE 2

| 10× T4 DNA polymerase buffer | 5 ul |
|---|---|
| 1 mg/ml BSA | 5 ul (100 ug/ml) |
| DNA | 15 ul (1.7 ug) |
| T4 polymerase | 1 ul (5 unit) |
| NFW (distilled water) | 19 ul |
| Total | 45 ul |

Then, prepared centrifuge tubes were reacted for 5 mins at a room temperature. 2 mM dNTPs 5 ul was added to the centrifuge tubes and it was further reacted for 5 mins at a room temperature, and phenol/chloroform (for DNA) 500 ul was added, thereby stopping reaction. Then, after adding 500 ul distilled water to centrifuge tubes and voltexing for 30 secs, the supernatant was removed by centrifuging for 5 mins at 10000 g at a room temperature, and after adding chloroform as the same volume with removed supernatant and voltexing for 30 secs, the supernatant was removed again by centrifuging for 5 mins at 10000 g at a room temperature, and after 3M NaOAC solution (pH 5.5) was added as much as 1/10 volume of DNA solution and 100% ethanol as much as 2.5 volume was added, it was voltexed and stored at −70° C. for 16 hrs.

Then, the solution was taken out on ice and centrifuged for 5 minutes at 10000 g, thereby removing supernatant to leave only the precipitate, and after adding 70% ethanol 1 ml and washing centrifuge tubes, the supernatant was removed by centrifuging for 5 mins at 4° C. at 10000 g. After adding 100% ethanol 1 ml and washing centrifuge tubes again, it was centrifuged for 5 mins at 4° C. at 10000 g, and the supernatant was removed. Then, after drying precipitate for 10 mins in Speed Vac (Jeio Tech), they were dissolved in 32 ul distilled water, and the purity and amount of DNA was measured using Nanodrop (Thermo Scientific, USA). As a result, it was demonstrated that the purity was approximately 2.0 as an OD260/OD280 value, and the concentration of fragmented DNA was over 50 ng/uL.

Example 3. Construction of a Genome-Originated Artificial ncRNA Expression Plasmid 3-1. Connection Reaction and Transformation The RNA expression plasmid DNA prepared in Example 1 and DNA fragments prepared in Example 2 were mixed to be below 4 uL of final volume and 1:150 as a molar concentration. Then, 5 uL 2× Rapid Ligation buffer solution (Promega, USA, C6711; 60 mM Tris-HCl, pH 7.8, 20 mM MgCl$_2$, 20 mM DTT, 2 mM ATP and 10% PEG), 1 uL T4 ligase (Enzynomics, KOREA, M019) were added and distilled water was filled to 10 uL, and DNA fragments were combined to the plasmid by reacting at 4° C. for 10 hrs.

Then, after mixing 1 to 2 uL reaction solution comprising the plasmid that DNA fragments were combined with 50 uL of DH5a competent cell (Enzynomics, Korea, CP010) and putting on ice for 20 mins, it was transformed by giving thermal shock for 1 min in a 42° C. constant temperature water bath and leaving it for 2 mins on ice.

3-2. Confirmation of Ligation Efficiency and Size of Inserted DNA 1 mL of LB medium (NaCl 1.0 g, yeast extract 0.5 g, and tryptone 1.0 g were dissolved in 100 mL distilled water) was added to the reaction solution comprising E. coli transformed in Example 3-1, and 300 uL of the shaking cultured solution was spread on LB/Ap agar medium (Micro agar (Duchefa, Nederland, M1002) 1.5 g was added to 100 ml LB medium to be 100 ug/mL of concentration of ampicillin) plate, and it was further cultured in a 37° C. incubator overnight.

Then, in order to confirm whether the connection reaction occurred well, after selecting 15 transformed E. coli colonies randomly and mixing solution under conditions as the following table 3 in a PCR reaction tube, colonies selected randomly were put one by one. After reacting the solution at 95° C. for 5 mins using PCR equipment, reaction of 95° C. 30 secs, 60° C. 30 secs, 72° C. 30 secs was repeated 30 times, and then it was reacted at 25° C. for 5 mins. Reaction products were analyzed by electrophoresis in an agarose gel and shown in FIG. 2.

TABLE 3

| | |
|---|---|
| Forward primer (SEQ ID NO: 2) | 0.5 ul (10 pmol/ul) |
| Reverse primer (SEQ ID NO: 3) | 0.5 ul (10 pmol/ul) |
| 2x prime taq pre mix | 10 ul |
| NEW | 9 ul |
| Total | 20 ul |

Figure 2:
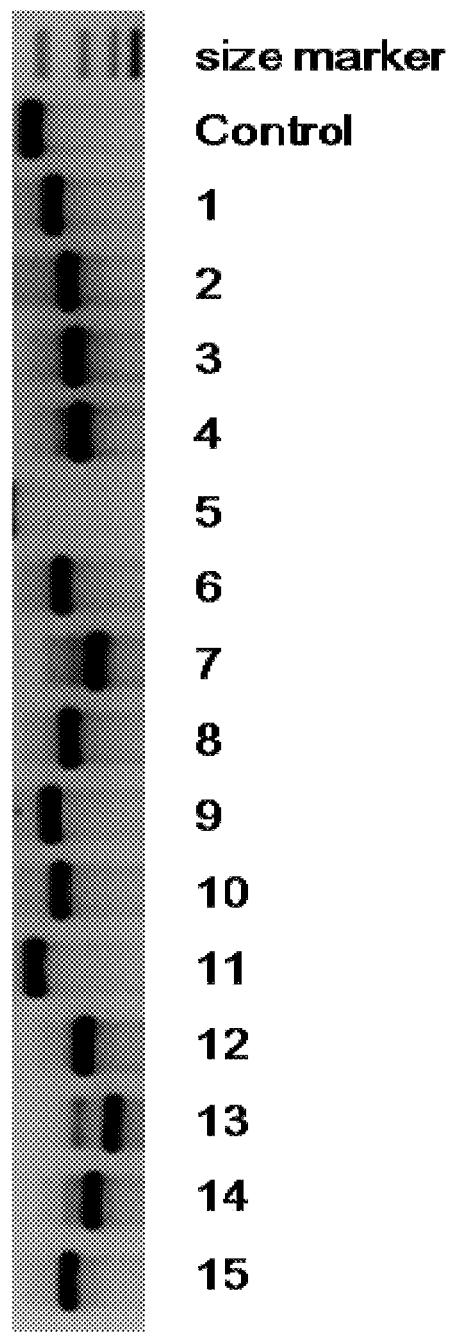
FIG. 2 is a photograph showing electrophoresis results of colony PCR products to analyze connection efficiency of RNA expression plasmid DNA and genome-originated DNA fragments according to one example of the present invention.

As can be seen in FIG. 2, it was demonstrated that DNA fragments were inserted well by colony PCR. Specifically, Control showed a size of PCR product in RNA scaffold that DNA fragments were not inserted, and 1 to 15 showed a size of PCR product obtained by selecting 15 transformed E. coli colonies randomly and conducting PCR. In other words, the difference of length of the two represented the length of DNA fragments which were inserted to RNA scaffold, and it can be demonstrated that appropriate length of DNA fragments were inserted well in the rest except for 5.

3-3. Scale Up of Connection Reaction 5 identical connection reactants under the condition of Example 3-1 were prepared. Then, 5 connection reactants were collected all together and phenol/chloroform (for DNA) 500 ul was added. After adding 500 ul nuclease free water to centrifuge tubes and voltexing for 30 secs, the supernatant was removed by centrifuging for 5 mins at 10000 g at a room temperature, and after adding chloroform as 1:1 with supernatant and voltexing for 30 secs, the supernatant was removed again by centrifuging for 5 mins at 10000 g at a room temperature, and after 3M NaOAC solution (pH 5.5) was added as much as 1/10 volume of the supernatant. 100% ethanol as much as 2.5 volume was added to the solution, it was voltexed and stored at −70° C. for 16 hrs.

Then, the solution was taken out on ice and centrifuged at 4° C. at 10000 g for 5 mins, thereby removing supernatant to leave only the precipitate, and after adding 70% ethanol 1 ml and washing centrifuge tubes, the supernatant was removed by centrifuging at 4° C. at 10000 g for 5 mins. After adding 100% ethanol 1 ml and washing centrifuge tubes again, it was centrifuged for 5 mins at 4° C. at 10000 g, and the supernatant was removed. Then, after drying precipitate for 10 mins in Speed Vac (Jeio Tech), they were dissolved in 100 ul distilled water, and the purity and amount of DNA was measured using Nanodrop (Thermo Scientific, USA). As a result, it was demonstrated that the purity was approximately 2.0 as an OD260/OD280 value, and the concentration of DNA was over 100 ng/uL.

3-4. Collection of Transformed E. coli Colonies

E. coli was transformed by electroporation using connection products obtained in Example 3-3.

1 mL of LB medium (NaCl 1.0 g, yeast extract 0.5 g, and tryptone 1.0 g were dissolved in 100 mL distilled water) was added to the reaction solution and 500 uL of the shaking cultured solution was spread on 20 plates containing LB/Ap agarmedium (Micro agar (Duchefa, Nederland, M1002) 1.5 g was added to 100 ml LB medium to be 100 ug/mL of concentration of ampicillin) in a 150 mm petri dish, respectively, and it was further cultured in a 37° C. incubator overnight. Transformed colonies were collected by adding LB 5 ml to each plate.

3-5. Purification of Plasmid DNA

Plasmid DNA was collected in cells of colonies obtained from Example 3-4 using plasmid DNA purification kit (Intron Biotechnology, Korea, 17096) according to the manufacturer's protocol. Collected plasmid DNA is a plasmid library that can express E. coli genome-originated artificial ncRNA.

Figure 3:
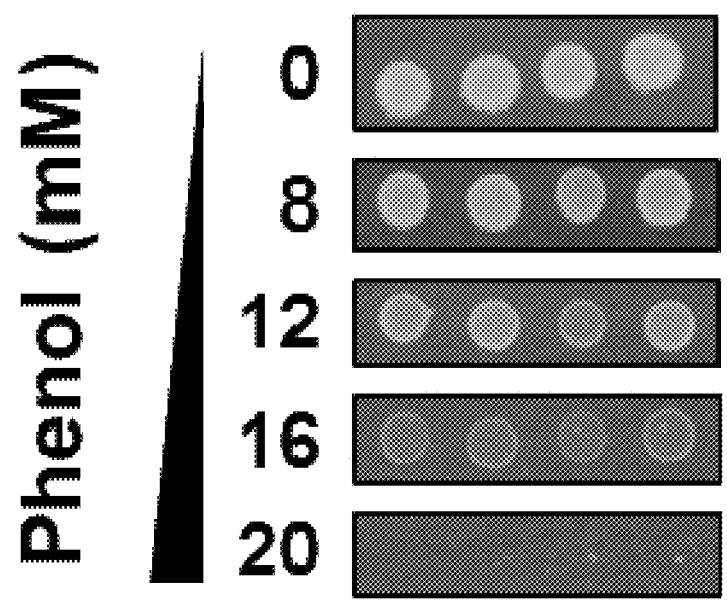
FIG. 3 is a photograph showing experimental results measuring MIC values to phenol of *E. coli* according to one example of the present invention.

Example 4. Development of an Artificial ncRNA with Improved Resistance to Phenol 4-1. MIC Measurement In order to measure MIC (minimal inhibitory concentration) to phenol of E. coli, E. coli MG1655 strain was spread to LB plate medium comprising phenol as much as ~$10^5$ cfu (colony forming unit) and cultured at 37 t for 16 hrs, and the result was shown in FIG. 3. As can be seen in FIG. 3, it is demonstrated that growth was totally inhibited at 20 mM of phenol concentration.

4-2. Screening of E. coli Living in Phenol MIC in Transformed E. coli

Figure 4:
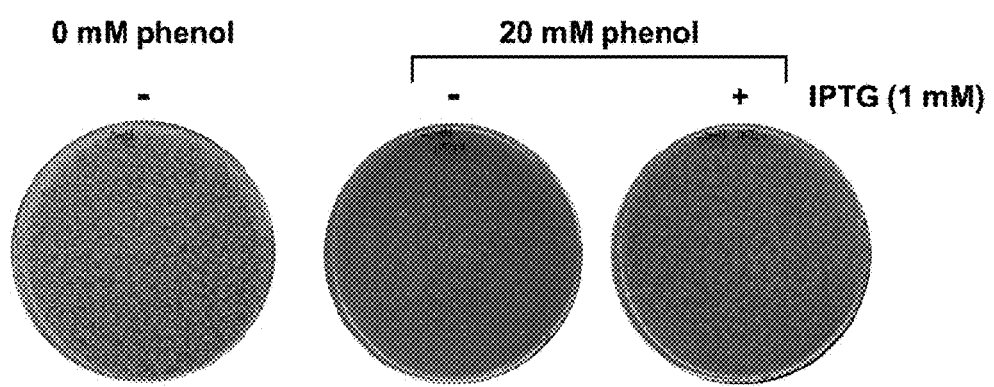
FIG. 4 is a photograph showing results of increasing survival of a cell in the condition of 20 mM phenol depending on the presence of IPTG which induces an artificial ncRNA expression according to one example of the present invention.

In order to develop an artificial ncRNA to make E. coli survived at 20 mM of phenol concentration, E. coli MG1655 was transformed by the plasmid library which can express genome-originated artificial ncRNA constructed in the Examples 3-5, and it was confirmed whether transformed ~500,000 colonies were survived in a LB plate comprising 1 mM IPTG, and the result was shown in FIG. 4.

As can be seen in FIG. 4, it was demonstrated that approximately 500 (~0.1%) colonies were survived. After collecting survived clones, 13 clones that the survival degree under 20 mM phenol varied greatly were developed depending on IPTG.

4-3. Analysis of DNA Nucleotide Sequences and Analysis of Target Gene of an Artificial ncRNA Plasmid DNA of 13 clones that resistance to phenol under 20 mM phenol condition was improved was purified, and nucleotide sequence part of E. coli genome in an artificial ncRNA was confirmed by analysis of nucleotide sequences, thereby demonstrating 9 kinds of artificial ncRNAs improving resistance to phenol.

In addition, in order to confirm a target gene that the confirmed artificial ncRNA act on, a target gene was predicted using Target RNA 2 web-based program. Specifically, target gene candidates for each anti-sense RNA nucleotide sequence were sorted as follows under the searching condition of 9 or 10 or more initial base pairs in the region of −30~+10 nt based on initiation codon of mRNA, and were shown in the following table 4.

TABLE 4

| SEQ ID NO: | Sequence listing (5'→3') | clone No. | Target gene |
|---|---|---|---|
| SEQ ID NO: 4 | AGGCAAGAAAAAAGCAAAAGTTCT | #P1, 12 | ygbI, caiD |
| SEQ ID NO: 5 | GATCGGCAGCAAAAGTTTGTGT | #P2 | ygbI |
| SEQ ID NO: 6 | TCCCAGACGTTTCCAGCGGTTGACGATTTCACAAAACAGCACAGCAGTGCGTTCGGTGTCGTA | #P3 | ygbG, yfeK |
| SEQ ID NO: 7 | GCCATCAATAAAATCCAGCACTCACAT | #P4, 7, 10, 13 | yohP, fabA, csgD, arpA |
| SEQ ID NO: 8 | CAACGAACCACCGGTTGCCACCACC | #P5 | thiI |
| SEQ ID NO: 9 | GCCACCGGCTACCAGCACAGCACGG | #P6 | yddW, ddpA |
| SEQ ID NO: 10 | AAACTACCAGCAAAACATAAATCCCCAC | #P8 | dmiR, opgG |
| SEQ ID NO: 11 | ACCGCTTCCCTTAATAGGTCCGCACGAGGA | #P9 | aroP, sapA |
| SEQ ID NO: 12 | TTTTACCCAGCCCAACAATCTCCCCACATATCCCGCTATCATTACCGTTTTCCTCCAGC | #P11 | Lit, avtA, entF |

As can be seen in table 4, it was demonstrated that target candidate genes are likely to be involved in a regulatory mechanisms that can increase resistance to phenol.

Example 5. Development of an Artificial ncRNA with Improved Resistance to Cinnamaldehyde

5-1. MIC Measurement

Figure 5:
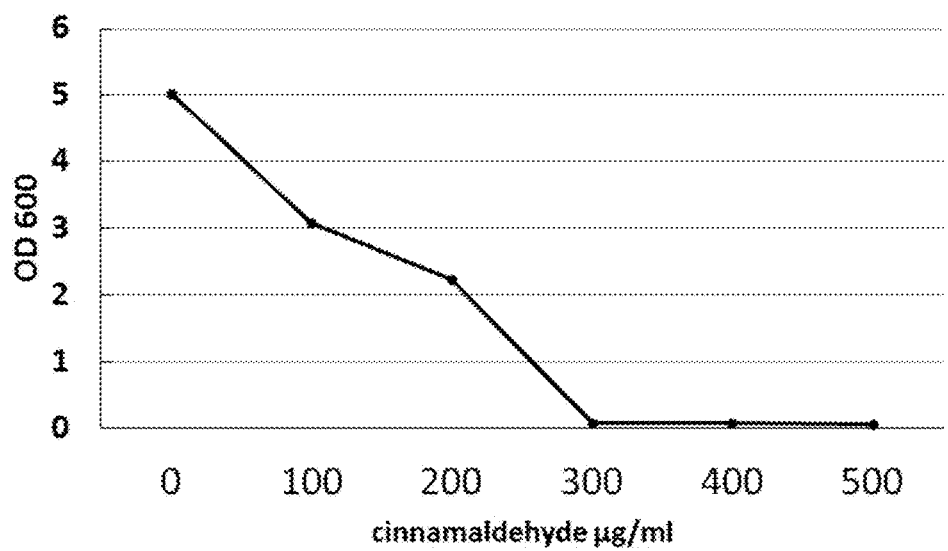
FIG. 5 is a graph showing experimental results of measuring MIC values to cinnamaldehyde of *E. coli* according to one example of the present invention.

In order to measure MIC (minimal inhibitory concentration) to cinnamaldehyde of E. coli, E. coli YHP05 strain which was fully grown in a LB liquid medium comprising cinnamaldehyde in a day was diluted to 1/100, cultured and inoculated, and cultured at 37° C. for 16 hrs, and the result was shown in FIG. 5 and table 5.

TABLE 5

| ug/ml | OD600 |
|---|---|
| 0 | 5.02 |
| 100 | 3.08 |
| 150 | 2.74 |
| 200 | 2.25 |
| 250 | 0.341 |
| 300 | 0.091 |
| 400 | 0.083 |
| 500 | 0.062 |

As can be seen in FIG. 5 and table 5, it was demonstrated that cells were not grown at 300 ug/ml cinnamaldehyde.

5-2. Screening of E. coli Living in Cinnamaldehyde MIC in Transformed E. coli In order to develop an artificial ncRNA to make E. coli survived at 300 ug/ml of cinnamaldehyde concentration, E. coli YHP05 was transformed by the plasmid library which can express genome-originated artificial ncRNA constructed in the Example 3-5, and after transformed ~500,000 colonies were cultured for 16 hrs, they were diluted to 1:100 and cultured for 16 hrs again in a LB medium comprising 350 ug/ml cinnamaldehyde, 1 mM IPTG, and the result was shown in FIG. 6 and table 6.

TABLE 6

|  | OD600 | Error bar |
|---|---|---|
| 1 | 0.561 | 0.3098806 |
| 2 | 0.845 | 0.1661144 |
| 3 | 0.503 | 0.0376563 |
| 4 | 0.2603333 | 0.0686553 |
| 5 | 0.273 | 0.0440984 |
| 6 | 0.2756667 | 0.0804418 |
| 7 | 0.411 | 0.0863018 |
| 8 | 0.32 | 0.0576021 |
| 9 | 0.2403333 | 0.1247967 |
| 10 | 0.28 | 0.0535226 |
| 11 | 0.3606667 | 0.0780185 |
| 12 | 0.309 | 0.1541882 |
| 13 | 0.1293333 | 0.0394152 |
| 14 | 0.182 | 0.0877534 |
| 15 | 0.2293333 | 0.0766565 |
| 16 | 0.1736667 | 0.1001011 |
| 17 | 0.247 | 0.1062168 |
| 18 | 0.2883333 | 0.1322657 |
| 19 | 0.277 | 0.1233396 |
| 20 | 0.1166667 | 0.0189268 |
| control | 0.0873333 | 0.0033993 |

Figure 6:
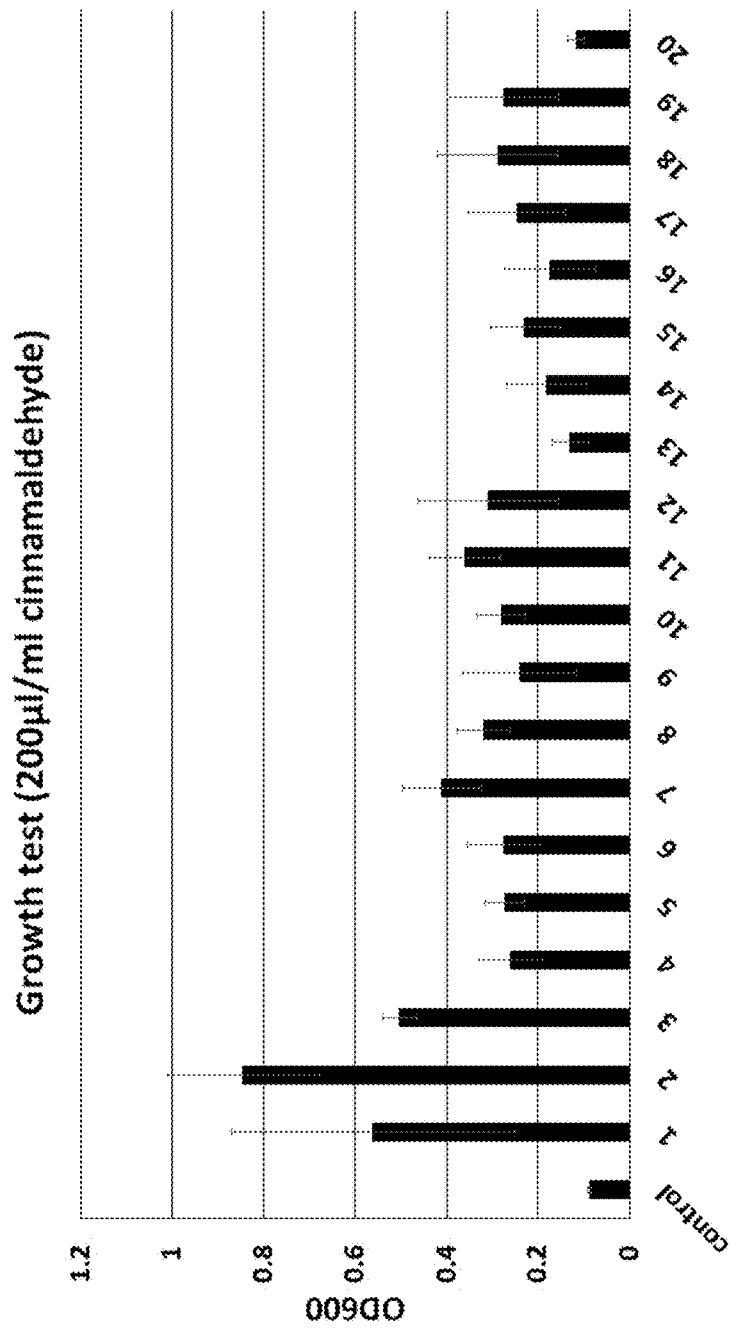
FIG. 6 is a graph showing survival increases in the presence of 200 ug/ml cinnamaldehyde when an artificial ncRNA is expressed according to one example of the present invention.

As can be seen in FIG. 6 and table 6, it was demonstrated that 20 clones were survived when culture solution was spread in a LB plate, and 20 clones that the survival degree under 200 ug/ml cinnamaldehyde varied greatly were confirmed depending on IPTG.

5-3. Analysis of DNA Nucleotide Sequences and Analysis of Target Gene of an Artificial ncRNA Plasmid DNA of 20 clones that resistance to cinnamaldehyde was improved was purified, and nucleotide sequence part of *E. coli* genome in an artificial ncRNA was confirmed by analysis of nucleotide sequences as follows. As a result of analysis of nucleotide sequences, 19 kinds of artificial ncRNAs improving resistance to cinnamaldehyde were collected.

In addition, if an artificial ncRNA acts gene silencing, a target gene can be predicted. A target gene for clones 1, 2 and 3 that their effects to improve resistance to cinnamaldehyde were the highest among 19 clones was predicted using Target RNA 2 web-based program. Specifically, target gene candidates for each anti-sense RNA nucleotide sequence were sorted under the searching condition of 11 or more initial base pairs in the region of −30~+10 nt based on initiation codon of mRNA, and were shown in the following table 7.

TABLE 7

| SEQ ID NO: | Sequence listing (5'→3') | clone No. | Target gene |
|---|---|---|---|
| SEQ ID NO: 13 | AATCAGCGGTTTTTGTGGAATGGCAAG GTTGTTAGATA | #A1 | priA, potF, yegR, caaA |
| SEQ ID NO: 14 | TGTTTGACCGCCCCTGTTTTTTAGCGTC AGGCATGATGCCCTCCAATATGGTTATT TTTTATTGTGAATTAAGATAGGTGAGTA CGACGTAAAAGATGTGAAGC | #A2 | ppdD, yeeD |
| SEQ ID NO: 15 | ACAGTTTCGCTTGGTGGTTTCTCAACTC ATAGCGAGAGTATCGGATATTTTACATG CCGACAACTTCGCCATCAAGCAGCGCC AGATGGTAGCGCATGTTTGGGTCGCGC AGATTGGCGTTAAAACCCACGCGAAAC GCGTGGTGGTCAAACTCCGCCTGTTTTA GCTCACAAATCAGCG | #A3 | mazE |
| SEQ ID NO: 16 | TGAGCAGTGATTTTCAGCTTATCGCCGG AACGGTGCGCGATTTGCGCC | #A5 | |
| SEQ ID NO: 17 | TATTCATTGCTTCTACCCGTGCCTCGCTT TCTGTATTACGAAATTGTCCCAACACAT GTGCCAGCCGATAAAAACCCAC | #A6 | |
| SEQ ID NO: 18 | AACGCAGGGCGTTCGAAAGCAGGTTGC TTAGCGCCCGACGCAGCATCAGCGGAT CGCCCGCGACCTGACACTTGTCGCCAAC AAACCGCAACTCCACGCCGCGATCTTCC GCTAACGCCTCGAAAAAATCGAACACT TTGCCGACTTCATCCGCCAG | #A7 | |
| SEQ ID NO: 19 | AATCCCTCAATGATGCCTGGAATCGCTC TTTTA | #A8 | |
| SEQ ID NO: 20 | GGCGCTGCATCCGCGTTATAGCCGCGCC CAGTATGACCGGGTAATGGA | #A9 | |
| SEQ ID NO: 21 | TCCACCATTTCGGAGAGTTTTTTACGCG CCAGCGGGCGGCT | #A10 | |
| SEQ ID NO: 22 | ATTACTGCGCCAGTTGAGGCCCTGGGTT TTGAACTGGTTGGCATCGAATTTATTCG CGGTCGCACATCCAC | #A11 | |
| SEQ ID NO: 23 | CCCTTCGCCAACAATCCCGGAGAGCGC CACAGCATCGGTCGGAGAAAGCACCGC CGCCAGCGCAAAGGCAGGG | #A12 | |
| SEQ ID NO: 24 | GGGCAAGGGCAAACATTTGCGGGT | #A13 | |
| SEQ ID NO: 25 | ACCGTCATAACGCGGCTTCTCACCTTTC GCCATTTGCTCT | #A14 | |
| SEQ ID NO: 26 | CCCACGGTGACGGGCATT | #A15 | |
| SEQ ID NO: 27 | AACAAAATATTCCGCGCGCTGTGCGGC CCACTTGGCGGCATAATCACCACCTACA GCAAAGTGAAATCCCCTACCCGCGTGA TCCAAATCCTTTCCGTACTCGGCCTGCT GAC | #A16 | |
| SEQ ID NO: 28 | AACAAAATATTCCGCGCGCTGTGCGGC CCACTTGGCGGCATAATCACCACCTACA GCAAAGTGAAATCCCCTACCCGCGTGA TCCAAATCCTTTCCGTACTCGGCCTGCT GAC | #A17 | |

TABLE 7-continued

| SEQ ID NO: | Sequence listing (5'→3') | clone No. | Target gene |
|---|---|---|---|
| SEQ ID NO: 29 | CCCTCCGGCAGTTGGAAGTTTTTGCAGAAGTATTGAAAAGTGGATCAACCACCCAGGC | #A18 | |
| SEQ ID NO: 30 | CTCCATCTTATTCCATCAGGTATTCTCCGCGAGAATGTAACCAGCATCATCGGTAACGGTGTTGTGCTGTCTCCGGCCGCGCTGATGAAAGAGA | #A19 | |
| SEQ ID NO: 31 | CCGGGAATTCAAAACCTCGCGGCAAACCATTTTAAGAGCCAAAGCAAAACTTCAGA | #A20 | |

The target candidate genes are likely to be involved in regulatory mechanisms that can increase resistance to cinnamaldehyde.

The invention claimed is:

1. A method for preparing an artificial ncRNA expression library comprising:
   preparing a random fragmented DNA that randomly fragments whole genome DNA;
   making a terminal end of the random fragmented DNA a blunt end;
   preparing an artificial ncRNA expression plasmid by connecting the DNA fragment with the blunt end to a plasmid DNA comprising the nucleotide sequence of SEQ ID NO: 1, which includes a double stem-loop type of RNA scaffold encoding sequence and a restriction enzyme site;
   transforming a cell by the artificial ncRNA expression plasmid; and
   constructing an artificial ncRNA expression library by purifying the artificial ncRNA expression plasmid from the transformed cell.

2. The method of claim 1, wherein the whole genome is derived from *E. coli*.

3. The method for preparing an artificial ncRNA expression library of claim 1, wherein the plasmid DNA is prepared by treating a plasmid with a restriction enzyme; and treating with phosphatase.

4. The method of claim 1, wherein the length of random fragmented DNA is regulated by controlling concentration of manganese ions, and time and temperature of DNase treatment.

5. The method of claim 4, wherein the random fragmented DNA is prepared by treating the whole genome DNA at the concentration of manganese ions of 5 to 15 mM, and at 15 to 25° C. for 5 to 7 minutes.

6. The method of claim 1, wherein the terminal blunt end of random fragmented DNA is prepared by decomposing 3' overhang of the random fragmented DNA and filling 5' overhang.

7. The method of claim 6, wherein the step of making a random fragmented DNA terminal a blunt end is filling 5' overhang by adding only dNTP without replacing reaction solution after decomposing 3' overhang.

8. The method of claim 1, further comprising a step of evaluating the library construction by conducting colony PCR reaction, after the step of constructing an artificial ncRNA expression library.

9. The method of claim 8, wherein the PCR reaction is conducted by using a primer pair consisting of nucleotide sequences of SEQ ID NO: 2 and SEQ ID NO: 3.

10. The method of claim 9, wherein the evaluation of the library construction is conducted by investigating a size of an artificial ncRNA.

11. The method of claim 1, wherein the random fragmented DNA has a length of 10 to 100 bases.

12. A method for screening an artificial ncRNA, wherein the method improves resistance to stress of cell by transforming a cell by the artificial ncRNA expression library prepared by the method of claim 1 and inducing artificial ncRNA expression.

* * * * *